(12) United States Patent
Schilling et al.

(10) Patent No.: US 12,194,012 B2
(45) Date of Patent: Jan. 14, 2025

(54) PREPARATION COMPRISING A DISPERSION OF PHOSPHOLIPIDS AND FATTY ACID SALTS

(71) Applicant: Evonik Operations GmbH, Essen (DE)

(72) Inventors: Martin Schilling, Bonn (DE); Mario Gomez, Darmstadt (DE); Bodo Speckmann, Kahl (DE); Anne Benedikt, Frankfurt (DE); Christian Kessler, Aschaffenburg (DE); Norbert Windhab, Hofheim (DE); Ines Ochrombel, Essen (DE)

(73) Assignee: Evonik Operations GmbH, Essen (DE)

( * ) Notice: Subject to any disclaimer, the term of this patent is extended or adjusted under 35 U.S.C. 154(b) by 760 days.

(21) Appl. No.: 17/294,835

(22) PCT Filed: Nov. 28, 2019

(86) PCT No.: PCT/EP2019/082919
§ 371 (c)(1),
(2) Date: May 18, 2021

(87) PCT Pub. No.: WO2020/109472
PCT Pub. Date: Jun. 4, 2020

(65) Prior Publication Data
US 2022/0016065 A1 Jan. 20, 2022

(30) Foreign Application Priority Data
Nov. 30, 2018 (EP) ..................................... 18209472

(51) Int. Cl.
*A61K 31/202* (2006.01)
*A23K 20/158* (2016.01)
(Continued)

(52) U.S. Cl.
CPC .......... *A61K 31/202* (2013.01); *A23K 20/158* (2016.05); *A23L 33/12* (2016.08);
(Continued)

(58) Field of Classification Search
CPC ...... A61K 31/202; A61K 47/24; A61K 47/14; A61K 9/127; A61K 8/553; A61K 9/1075; A61K 9/0014; A61K 8/9789; A61K 2300/00; A61K 9/0053; A61K 8/9794; A61K 2800/262; A61K 2800/31; A61K 2800/413; A61K 47/12; A61K 8/0208; A61K 8/0291; A61K 8/042; A61K 8/442; A61K 8/463; A61K 8/4993; A61K 8/63; A61K 8/64; A61K 8/86; A61K 8/9767; A61K 8/9771; A61K 9/14; A61K 9/48; A61K 47/08; A61K 8/0241; A61K 8/33; A61K 8/37; A61K 31/685; A61K 45/06; A61K 9/1277; A61K 31/20; A61K 9/4858; A61K 2236/00; A61K 2236/331; A61K 2236/37; A61K 2236/53; A61K 31/683; A61K 35/612; A61K 36/324; A61K 47/36; A61K 9/00; A61K 9/145; A61K 31/122; A61K 31/215; A61K 31/23; A61K 31/235; A61K 31/575; A61K 47/183; A61K 9/16; A61K 9/1617; A61K 9/20; A61K 9/4825; A61K 31/201; A61K 35/742; A61K 9/107; A61K 9/0029; A61K 9/0048; A61K 31/197; A61K 47/38; A61K 9/1274; A61K 2800/92; A61K 8/0216; A61K 8/922; A61K 8/925; A61K 9/2095; A61K 31/557; A61K 2800/75; A61K 38/4873; A61K 8/066; A61K 8/14; A61K 8/416; A61K 8/42; A61K 8/44; A61K 8/447; A61K 8/55; A61K 8/676; A61K 8/8147; A61K 8/8164; A61K 8/90; A61K 9/0056; A61K 9/146; A61K 9/2013; A61K 9/2018; A61K 9/4833; A61K 9/4866; A61K 9/4875; A61K 31/22; A61K 31/232; A61K 9/0019;
(Continued)

(56) References Cited
U.S. PATENT DOCUMENTS
5,015,483 A 5/1991 Haynes et al.
5,750,572 A 5/1998 Bruzzese
(Continued)

FOREIGN PATENT DOCUMENTS
CN 107105746 A 8/2017
EP 0245723 A2 * 11/1987 ............... A21D 2/32
(Continued)

OTHER PUBLICATIONS
International Search Report and Written Opinion issued on Apr. 1, 2020 in PCT/EP2019/082919 filed on Nov. 28, 2019.
(Continued)

*Primary Examiner* — Audrea B Coniglio
(74) *Attorney, Agent, or Firm* — Oblon, McClelland, Maier & Neustadt, L.L.P.

(57) ABSTRACT

A preparation containing a mixture of at least one phospholipid, and at least one fatty acid salt of a cation with an anion derived from a fatty acid. A method for preparing such preparation and the use of such preparation to provide polyunsaturated fatty acids to cells, tissues, organs or organisms, for example in the field of cell and tissue culture, organ preservation, human or animal nutrition, or cosmetics.

18 Claims, No Drawings

(51) Int. Cl.
*A23L 33/12* (2016.01)
*A61K 9/127* (2006.01)
*C12N 5/077* (2010.01)

(52) U.S. Cl.
CPC .......... *A61K 9/1277* (2013.01); *C12N 5/0652* (2013.01); *C12N 2500/30* (2013.01)

(58) Field of Classification Search
CPC ........ A61K 47/10; A61K 47/44; A61K 31/05; A61K 31/085; A61K 31/09; A61K 31/138; A61K 31/167; A61K 31/216; A61K 31/352; A61K 31/381; A61K 31/4025; A61K 31/415; A61K 31/421; A61K 31/4535; A61K 31/4704; A61K 31/4709; A61K 31/4745; A61K 31/55; A61K 47/22; A61K 31/231; A61K 31/192; A61K 31/40; A61K 31/616; A61K 9/0095; A61K 9/06; A61P 3/10; A61P 9/00; A61P 25/00; A61P 3/04; A61P 3/08; A61P 43/00; A61P 11/06; A61P 11/00; A61P 17/00; A61P 19/02; A61P 25/08; A61P 25/16; A61P 25/18; A61P 25/22; A61P 25/24; A61P 25/28; A61P 29/00; A61P 35/00; A61P 25/04; A61P 25/06; A61P 3/06; A61P 9/10; A61P 9/12; A61P 13/02; A61P 13/04; A61P 13/12; A61P 15/00; A61P 17/02; A61P 17/06; A61P 19/10; A61P 21/02; A61P 25/20; A61P 25/32; A61P 27/02; A61P 3/14; A61P 1/04; A61P 1/16; A61P 21/00; A61P 25/14; A61P 25/30; A61P 25/34; A61P 25/36; A61P 27/00; A61P 27/06; A61P 3/00; A61P 35/02; A61P 37/06; A61P 37/08
See application file for complete search history.

(56) References Cited

U.S. PATENT DOCUMENTS

| | | | |
|---|---|---|---|
| 9,320,765 B2 * | 4/2016 | Bruheim | ................ A61K 31/20 |
| 2007/0042008 A1 * | 2/2007 | Kane | .................... A61K 31/685 |
| | | | 514/547 |
| 2017/0360072 A1 | 12/2017 | Knaup et al. | |

FOREIGN PATENT DOCUMENTS

| | | | | |
|---|---|---|---|---|
| WO | WO 2011/137160 A2 | 11/2011 | | |
| WO | WO2016102323 | * | 6/2013 | ........... A23L 33/105 |
| WO | WO 2016/102323 A1 | 6/2016 | | |
| WO | WO 2017/155396 A1 | 9/2017 | | |

OTHER PUBLICATIONS

English translation of combined Chinese Office Action and Search Report issued Dec. 7, 2023 in Chinese Application 201980078485.7, 15 pages.

Levental, K. et al., "w-3 polyunsaturated fatty acids direct differentiation of the membrane phenotype in mesenchymal stem cells to potentiate osteogenesis", Science Advances, vol. 3, 2017, pp. 1-15.

Office Action issued May 9, 2023, in corresponding Canadian Patent Application No. 3,121,055, 4 pages.

* cited by examiner

PREPARATION COMPRISING A DISPERSION OF PHOSPHOLIPIDS AND FATTY ACID SALTS

The invention describes compositions containing phospholipids and omega-3 fatty acid salts, formulations & processes to prepare such compositions in liposomal form and applications thereof.

Omega-3 fatty acids, especially dodecahexaenoic acid (DHA) and eicosapentaenoic acid (EPA) are known to have various beneficial effect on human health, are important building blocks of various cellular constituents and act as precursors for signaling molecules.

The main sources for these compounds are fish and algal oils as well as some plant derived oils, where they are present in the form of triglycerides. Various oils as well as the oil derived ethyl esters are commercially available.

Since daily consumption of these omega-3 sources with food or nutritional supplements is limited, it's important to assure maximum bioavailability of these fatty acids. Bioavailability of hydrophobic nutrients in the digestive system is often low and represents a challenge especially for supplements, because they are frequently consumed independently from a meal in the form of capsules or pills. Secretion of digestive fluids (bile acids, phospholipids, lipases) is hardly or not at all induced in the fasted state, which results in incomplete enzymatic hydrolysis of fats and oils, low solubilization and bioavailability.

An additional bioavailability challenges arise, when advanced formulation technologies are used to skip parts of the digestive systems in order to release omega-3 fatty acids in the lower part of the digestive system, e.g. in the small or large intestine. Capsules or tablets coated with respective release polymers can be used for this purpose. In these systems, the above mentioned, natural solubilization mechanisms are less effective, which reduces bioavailability and has to be compensated by appropriate measures.

The same is true for the supply of omega-3 fatty acids to isolated cells and tissues for in vitro cultivation, e.g. as part of a serum-free cell culture medium compositions. In those applications, solubilization in the digestive tract is preferably mimicked by formulations that are close to the natural system to maximize biocompatibility and bioavailability. For the addition to cell culture media, it is also essential that the fatty acids are dispersed in the medium in a way that allows optimum passage through sterile filters.

Various approaches have been developed to solve the bioavailability problem, either by formulation, chemical modification of omega-3 fatty acids or both.

One promising approach is the hydrolysis and subsequent saponification of omega-3 fatty acid esters, which mimics part of the natural digestive process and thereby increases solubility. WO2016102323A1 describes compositions comprising polyunsaturated omega-3 fatty acid salts that can be stabilized against oxidation.

Formulation can also improve bioavailability. For example, WO2010103402 discloses self-emulsifying oil formulations containing surfactants have been shown to increase dispersion in the stomach and increase bioavailability. The drawback of such systems is that they normally require non-ionic, synthetic surfactants that are not sustainably sourced and less and less accepted by the consumer. Another drawback is the high amount of surfactant and cosurfactant relative to the oil or ethyl ester required to generate fine oil droplets after dispersion in water. Finally, these systems are still in a liquid state, which renders them prone to oxidation and usually requires addition of antioxidants and special precautions with regard to processing and packaging.

Phospholipids, such as phosphatidylcholine (lecithin), are natural amphiphiles and food ingredients that are highly biocompatible and easily digestible. They have been used as emulsifiers in the food industry and as nutritional supplements for many decades. Therefor it is not surprising, that phospholipids have been used to formulate omega-3 fatty acid forms. For example, Alaarg et al. (International Journal of Nanomedicine 2016:11 5027-5040) and Hadian et al. (Iranian Journal of Pharmaceutical Research (2014), 13 (2): 393-404) have prepared phospholipid based, liposomal formulations from omega-3 free fatty acids and esters.

However, phospholipid based, liposomal formulations of omega-3 esters and fatty acids also have several disadvantages. Omega-3 triglycerides and ethyl esters have such low polarity, that only low amounts can be stably dispersed in liposome bilayers. They are also difficult to convert to a more concentrated, powderous form by drying without addition of additional excipients due to the sticky character of the oil and some of the phospholipids. Use of free fatty acids requires neutralization of the free fatty acids, which complicates processing and can result in lower liposome quality and stability and also introduced counter-ions such as sodium or potassium (via NaOH or KOH), which are undesired in nutritional and other applications.

Surprisingly it was found, that omega-3 preparations that overcome the above mentioned problems can be prepared from mixtures of phospholipids with omega-3 fatty acid salts. Especially salts with basic amino acids as counter ions were found to have beneficial properties.

Therefore, one aspect of the present invention is a preparation comprising a dispersion of at least one phospholipid, and at least one fatty acid salt of a cation with an anion derived from an omega-3 or omega-6 fatty acid.

A dispersion according to the present invention is according to the IUPAC definition a material comprising more than one phase where at least one of the phases consists of finely divided phase domains, often in the colloidal size range, dispersed throughout a continuous phase. The two phases may be in the same or different states of matter. They are different from solutions, where dissolved molecules do not form a separate phase from the solute. The present invention is referring both to dispersions of a liquid phase in a liquid medium as colloid (miniemulsion or microemulsion) or as suspension (emulsion with particle size over 1 μm) and to dispersions of a solid phase in a liquid medium as colloid (sol) or as suspension (with p article size over 1 μm). Moreover, the invention is also related to a dispersion of a solid phase in a solid continuous medium, which is referred to as a solid sol.

A colloid is a dispersion with a dispersed phase between 1 nm and 1 μm and is defined as an emulsion when a liquid phase is dispersed in a liquid continuous medium, as a sol when a solid phase is dispersed in a liquid continuous medium and as a solid sol when a solid phase is dispersed in a solid continuous medium.

The preparation process of such dispersions could be improved and simplified. The compositions were found to have better quality and stability. The content of undesired inorganic counterions such as sodium could be reduced. Sterile filtration of the liquid forms was significantly facilitated by the inventive composition compared to other forms of omega-3 fatty acids. Dry powders prepared from the inventive compositions were found to have better properties, which facilitate processing.

It was also found that such formulations strongly improve bioavailability of omega-3 fatty acid for microbial and animal, including human cells.

The inventive compositions of the invention consist of phospholipids that are able to form bilayers and salts of omega-3 fatty acids, preferably amino acid salts of omega-3 fatty acids. Phospholipids can be complex mixtures (e.g. deoiled lecithin), defined backbones with variations in fatty acid composition (e.g. phosphatidylcholine, with unsaturated or hydrogenated fatty acids) or purified and defined compounds (e.g. dioleylphosphatidyl choline, DOPC).

In a preferred configuration of the present invention the fatty acid is selected from eicosapentaenoic acid (EPA), docosahexaenoic acid (DHA), arachidonic acid (ARA), alpha linolenic acid, stearidonic acid, eicosatetraenoic acid, docosapentaenoic acid, linoleic acid, γ-linolenic acid and/or derivatives thereof, preferably selected from the omega-3 fatty acids EPA and DHA.

In a further preferred configuration the cation in the fatty acid salt is an organic cation derived from one of the following: lysine, arginine, ornithine, choline and mixtures of the same.

In an alternative configuration of the present invention the phospholipid is a deoiled phospholipid comprising a phosphatidylcholine content of greater than 40 weight %, preferably 70 weight %, preferably greater 90 weight % and a phosphatidylethanolamine content of lower than 5 weight %, preferably lower than 1 weight %.

In an alternative embodiment the phospholipid is a non-hydrogenated phospholipid having an oleic and/or linoleic acid content of greater than 70 weight % of total fatty acids.

In a further preferred configuration of the present invention the mass ratio of phospholipid to fatty acid salt is greater than 0.005, preferably greater than 0.01, more preferably greater than 0.09, most preferably greater than 0.39.

In an alternative embodiment the preparation is in the form of a powder or of a liquid that result in colloidal dispersions with mean particle sizes of smaller than 1 μm, preferably smaller than 500 nm, most preferably smaller than 250 nm when mixed with water at a pH value between pH 6.5 and 7.5.

In another embodiment the components are finely dispersed in each other so that both phospholipid and fatty acid salts are present and detectable in amounts of 100 μg and smaller.

A further subject of the present invention is a culture medium, such as a cell culture medium, comprising a preparation according to any one of the preceding claims.

In a preferred embodiment the culture medium is in liquid form, in form of a gel, a powder, a granulate, a pellet or in form of a tablet.

In other preferred embodiments, the culture medium is a liquid medium in 2-fold, 3-fold, 3.33-fold, 4-fold, 5-fold or 10-fold concentrated form (volume/volume), relative to the concentration of said medium in use. This allows preparation of a "ready-to-use" culture medium by simple dilution of the concentrated medium with the respective volume of sterile water. Such concentrated forms of the medium of the invention may also be used by addition of the same to a culture, e.g., in a fed-batch cultivation process.

Another aspect of the present invention relates to a method for preparing a preparation according to the present invention, comprising at least the following steps:
a. Dissolving a phospholipid and a fatty acid salt together in a water-miscible solvent and adding small amounts of water to fully dissolve the salt;
b. Adding the solution to an aqueous system to prepare a lipid dispersion;
c. Reducing the particle size of the lipid dispersion to a mean particle size of smaller than 500 nm, preferably smaller than 250 nm, via sonification or homogenization;
d. Optionally drying the preparation, preferably via spray or freeze drying.

In an alternative embodiment of the method according to the present invention comprises at least the following steps:
a. Dissolving the phospholipid in a water-miscible solvent;
b. Dissolving the fatty acid salt in an aqueous system and adding the phospholipid solution to prepare a lipid dispersion;
c. Reducing the particle size of the lipid dispersion to a mean particle size of smaller than 500 nm, preferably smaller than 250 nm, via sonification or homogenization;
d. Optionally drying the preparation, preferably via spray or freeze drying.

In a preferred embodiment of the method according to the present invention the water-miscible solvent is selected from one or more of the following: ethanol, glycerol and propylene glycol.

Another aspect of the present invention relates to a use of a preparation according to the present invention to provide polyunsaturated fatty acids to cells, tissues, organs or organisms, preferably in the field of cell and tissue culture, organ preservation, human or animal nutrition, pharmaceutics or cosmetics.

In a specific embodiment is related to a use of a preparation according to the present invention for the cultivation and stimulation of expansion of mesenchymal stem cells.

An alternative embodiment refers to the use of a preparation according to the present invention as a feed or food supplement or as a pharmaceutical product.

A further subject of the present invention is a feed- or foodstuff composition containing a preparation according to the present invention and at least one further feed or food ingredient, preferably selected from proteins, carbohydrates, fats, further probiotics, prebiotics, enzymes, vitamins, immune modulators, milk replacers, minerals, amino acids, coccidiostats, acid-based products, medicines, and combinations thereof.

The feed- or foodstuff composition according to the present invention does also include dietary supplements in the form of a pill, capsule, tablet or liquid.

A further subject of the current invention is a pharmaceutical composition containing a preparation according to the present invention and a pharmaceutically acceptable carrier.

The preparations according to the present invention, when administered to animals or human beings, preferably improve the health status, in particular gut health, cardiovascular health, cardio-metabolic health, lung health, joint health, eye health, mental health, oral health or immune health of an animal or a human being.

A further subject of the current invention is therefore a composition according to the present invention for improving the health status, in particular gut health, cardiovascular health, cardio-metabolic health, lung health, joint health, eye health, mental health, oral health or immune health of an animal or a human being is part of the present invention.

WORKING EXAMPLES

The preparations of omega-3 fatty acids were characterized with the following methods:

1.1 Particle Size Determination

Particle size was determined via dynamic light scattering (DLS) measurements (Zetasizer Nano ZS, Malvern).

1.2 Turbidity Measurement

Turbidity of the preparations was measured after 100× dilution with water in a photometer at 600 nm in cuvettes with 1 cm light path.

1.3 Sterile Filtration Properties 5 ml of liquid preparations were filtered through a 0.2 µm sterile syringe filter. Ease of filtration was evaluated via increasing counter pressure or complete clogging. Turbidity measurement via photometry at 600 nm was evaluated before and after filtration. Higher turbidity is correlated with larger particle sizes. Reduction of turbidity is a sign of material loss through filtration, which is undesirable since the composition of the sample should be changed as little as possible.

1.4 Drying and Evaluation of Powder Properties

The preparations were freeze dried and the dry preparations were evaluated qualitatively with regard to consistency and flow behavior.

1 ml of the respective solutions was added dropwise to 20 ml of a 0.1 M phosphate buffer, pH=8, at a temperature of 45° C. and under intense stirring. pH was adjusted to pH=8 with NaOH if necessary. Afterwards the dispersion was put on ice and sonified (Branson Sonifier, 100% amplitude, 50% impulse) for 15 minutes to generate nanometer scale dispersions, presumably liposomes. The dispersions were sterile filtered through 0.2 µm syringe filters. Turbidity and particle size were measured before and after sterile filtration as described in 1.2. The preparation contained 40 g/l phospholipids and 10 g/l omega-3 fatty acids or esters. In a last step, the dispersions were freeze-dried and the appearance of the preparation obtained was analyzed visually.

Surprisingly it was found, that the preparations obtained with the omega-3 fatty acid lysine, arginine or ornithine salt had a smaller particle size, showed the best filtration properties and resulted a substantially less sticky powder after freeze-drying. The results for the triglyceride and ethyl ester as comparative example (comp.) and the fatty acid lysine, arginine and ornithine salts (according to the invention) are summarized in table 1.

TABLE 1

Properties of various omega-3 fatty acid dispersions with DOPC

| Composition | 1.1 (comp.) | 1.2 (comp.) | 1.3 (inv.) | 1.4 (inv.) | 1.5 (inv.) |
|---|---|---|---|---|---|
| Phospholipid | DOPC | DOPC | DOPC | DOPC | DOPC |
| Omega-3 fatty acid form | Triglyceride | Ethyl ester | Fatty acid lysine salt | Fatty acid arginine salt | Fatty acid ornithine salt |
| Mean particle size (nm) before sterile filtration | 168 | 148 | 132 | 97 | 95 |
| Turbidity before sterile filtration (AU) | 0.42 | 0.38 | 0.05 | n.d. | n.d. |
| Turbidity after sterile filtration (AU) | 0.25 | 0.17 | 0.04 | n.d. | n.d. |
| Reduction of turbidity by sterile filtration (AU) | 0.17 | 0.21 | 0.01 | n.d. | n.d. |
| Filtration performance | filter clogging | filter clogging | easy to filter | easy to filter | easy to filter |
| Properties of dried product (1 = sticky-4 = free flowing) | 1 | 1 | 3 | n.d. | n.d. |

Example 1: Preparation and Characterization of Omega-3 Fatty Acid Dispersions with Dioleylphosphatidylcholine (DOPC) in Phosphate Buffer To prepare formulations of omega-3 fatty acid dispersions 0.8 g of dioleylphosphatidylcholine (DOPC, Lipoid GmbH) were dissolved in 1 ml ethanol. 0.2 g of fish oil (Omega-3 1400, Doppelherz®), omega-3 ethyl ester (PronovaPure® 500:200 EE, BASF), lysine salt of free omega-3 fatty acid in form of omega-3 lysine salt (AvailOm®, Evonik), omega-3 fatty acid ornithine salt, or omega-3 fatty acid arginine salt were added and dissolved. The lysine salt did not dissolve in ethanol, but it was discovered that it could be dissolved when additionally 20 µl of distilled water were added.

The lysine salt of the free omega-3 fatty acid in form of omega-3 lysine salt (AvailOm®, Evonik) contains around 67% of fatty acids and high amounts of the omega-3 fatty acids EPA and DHA and small amounts of the omega-3 fatty acid docosapentaenoic acid and the omega-6 fatty acids arachidonic acid, docosatetraenoic acid and docosaenoic acid isomer.

Example 2: Preparation of Omega-3 Fatty Acids and Omega-3 Fatty Acid Lysine Salt Dispersions with DOPC in Water Formulations were prepared as described in example 1 except that water was used instead of phosphate buffer. In addition to omega-3 fatty acid lysine salt (AvailOm®, Evonik) the corresponding omega-3 free fatty acid was used to determine differences between the two forms. pH measurement with a pH electrode after addition of lipids to water showed that formulations with the free acid were rather acidic and had to be adjusted with NaOH before sonification to obtain proper dispersion whereas addition of the respective salts resulted in preparations with an appropriate pH that could be dispersed via sonification without addition of base. Surprisingly, the freeze-dried product containing the omega-3 fatty acid lysine salt (2.2) was better flowing and less sticky than the powder obtained from processing the omega-3 free fatty acid (2.1 comparative) and thus provides benefits regarding processing of such powders. The results are shown in table 2.

TABLE 2

Differences between compositions prepared with omega-3 free fatty acid and omega-3 fatty acid lysine salt.

| Composition | 2.1 (comp.) | 2.2 (inventive) |
|---|---|---|
| Phospholipid | DOPC | DOPC |
| Omega-3 fatty acid form | Free fatty acid | Fatty acid lysine salt |
| pH after addition of ethanolic lipid solution to water | 4.6 | 9.1 |
| Addition of NaOH (base) required to obtain neutral or alkaline pH | Yes | No |
| Properties of dried product (1 = oily, sticky-5 = free flowing) | 2 | 3 |

Example 3: Preparation and Characterization of Omega-3 Fatty Acid Lysine Salt Dispersions with DOPC at Various Ratios of Fatty Acid Salt to Phospholipid Formulations were prepared as described in example 1 except that water instead of phosphate buffer was used and different ratios of omega-3 fatty acid salt to phospholipid were used. The obtained aqueous dispersions all contained 10 g/l of omega-3 fatty acid salt but different concentrations of DOPC. An aqueous colloidal solution of omega-3 fatty acid salt without phospholipid was also prepared for comparison. 5 ml of the obtained dispersions were diluted in 45 ml of 20 mM phosphate buffer, pH=7, to evaluate dispersion properties at physiological pH via particle size and turbidity measurements. Turbidity of the diluted dispersions was measured in 96-well microtiter plates at 600 nm with a liquid volume of 100 µl in a microplate reader (Tecan Infinite 200 PRO). Surprisingly it was found, that already small amounts of DOPC were sufficient to improve dispersion of omega-3 fatty acid salt compared to the omega-3 fatty acid salt without added phospholipid. This could be demonstrated by reduced turbidity and smaller particle sizes. The results are summarized in table 3.

TABLE 3

Compositions with various DOPC omega-3 fatty acid lysine salt ratios, obtained particle size and turbidity after dilution of compositions at pH = 7 (n. d.: not determined)

| Composition | 3.1 | 3.2 | 3.3 | 3.4 | 3.5 | 3.6 |
|---|---|---|---|---|---|---|
| DOPC (g/l) | 40 | 20 | 10 | 4 | 1 | 0 |
| Omega-3 fatty acid lysine salt (g/l) | 10 | 10 | 10 | 10 | 10 | 10 |
| Ratio DOPC/omega-3 | 4 | 2 | 1 | 0.4 | 0.1 | — |
| Mean particle diameter (nm) after dilution at pH = 7 | 95 | 194 | 226 | 157 | 388 | n. d. |
| Absorbance (AU) at 600 nm after dilution at pH = 7 | 0.2 | 0.2 | 0.3 | 0.3 | 0.4 | 0.9 |

Example 4: Preparation and Characterization of Omega-3 Fatty Acid Dispersions with Lecithin in Water Formulations were prepared as described in example 3, except that 0.8 g of deoiled sunflower lecithin/phosphatidylcholine with a phosphatidylcholine content>90 weight % (Lipoid H 100) was used instead of DOPC. Dilutions in phosphate buffer at pH=7 were prepared and turbidity was measured as described in example 3. The results are shown in table 4 and were comparable to those obtained with DOPC. Already small amounts of phospholipid resulted in a much finer dispersion of the fatty acid salts at this pH value as indicated by a lower turbidity. The differences were also easy to observe visually. Whereas 4.6 appeared rather milky, the phospholipid containing compositions were almost transparent and only slightly turbid.

TABLE 4

Compositions with various lecithin omega-3 fatty acid lysine salt ratios, obtained particle size and turbidity after dilution of compositions at pH = 7

| Composition | 4.1 | 4.2 | 4.3 | 4.4 | 4.5 | 4.6 |
|---|---|---|---|---|---|---|
| Phosphatidylcholine Lipoid H100 (g/l) | 40 | 20 | 10 | 4 | 1 | 0 |
| Omega-3 fatty acid lysine salt (g/l) | 10 | 10 | 10 | 10 | 10 | 10 |
| Ratio Lipoid H100/omega-3 | 4 | 2 | 1 | 0.4 | 0.1 | |
| Absorbance (600 nm) after dilution at pH = 7 | 0.21 | 0.18 | 0.26 | 0.13 | 0.29 | 0.75 |

Example 5: Alternative Method to Prepare Omega-3 Fatty Acid Salt Dispersions with Dioleylphosphatidylcholine in Water It was found that preparations according to the invention can be prepared in a mixing sequence that simplifies the process and is not suitable for omega-3 fatty free fatty acid form or respective esters. Instead of dissolving the omega-3 fatty acid lysine salt with the phospholipid in ethanol it was directly dissolved in water at a concentration of 10 g/l and the ethanolic phospholipid solution was added subsequently. Afterwards the dispersion was sonified and sterile filtered as described in the previous examples.

Example 6: Stimulation of Production of 18-Hydroxy-Eicosapentaenoic Acid (18-HEPE) in the Strain *B. megaterium* DSM 32963

Due to their low polarity, the bioavailability of omega-3 fatty acids often is not sufficient and only low amounts are actually used and converted by cells in biochemical reactions. It could be shown, that the preparations described in this invention enhance bioavailability and metabolic conversion of omega-3 fatty acids of microbial cells, which is relevant in nutritional applications such as microbiome utilization and modulation.

*Bacillus megaterium* DSM 32963 has been identified by screening of naturally occurring isolates. It has been deposited with the DSMZ on Nov. 27, 2018 under the provisions of the Budapest Treaty on the International Recognition of the Deposit of Microorganisms for the Purpose of Patent Procedure under the Accession Number as mentioned before in the name of Evonik Degussa GmbH.

The preparations described in table 1 were added to microbial cultures of *Bacillus megaterium* DSM 32963 in liquid cultures in shake flasks. For comparison purposes, an omega-3 fatty acid lysine salt solution in water with the same omega-3 fatty acid concentration was also added. *Bacillus megaterium* DSM 32963 was found to catalyze the conversion of eicosapentaenoic acid (EPA) into bioactive 18-hydroxy-eicosapentaenoic acid (18-HEPE).

From 10 ml auf Luria Bertami broth (LB, Thermo Fisher Scientific) with 0.1% Glucose (LBG) a culture of *B. megaterium* DSM 32963 was grown for 24 h at 30° C. and 200 rpm in 100 ml flask. The complete culture was transferred to 200 ml main culture in LBG. Main culture was grown for 6 h at 30° C. and 200 rpm in a 2 l flask. The cell culture was then harvested in 10 ml portions, the supernatant removed by centrifugation (15 min, 4000 rpm, room temperature) and the cell pellet resuspended in 10 ml LBG or LBG containing 9.76 g/l FeSSIF-V2 (biorelevant.com), which is a mixture of taurocholate, phospholipids and other components designed to simulate bile surfactants, and 2 ml of lipid stock solutions were added, that were prepared from the sterile filtered preparations in example 2 to obtain the same EPA concentration in each experiment (table 5), respectively. Additionally, the supplements were also added respectively to the different media in shaking flasks without cells, and treated under the same conditions to control for non-biochemical product formation. These cultures & respective controls were incubated in 100 ml shaking flasks for 16 h at 30° C. and 200 rpm.

TABLE 5

Supplements, preparation of stock solutions, and its calculated EPA content (g/l)

| Preparation | Preparation of stock solution | EPA content calculated (g/l) |
| --- | --- | --- |
| Omega-3 lysine salt (preparation 4.6) | 0.6 g in 100 ml PBS buffer | 2.04 |
| Preparation of fish oil with DOPC (preparation 1.1) | undiluted | 2.04 |
| Preparation of omega-3 ethyl ester with DOPC (preparation 1.2) | 4.08 ml + 5.92 ml PBS buffer | 2.04 |
| Preparation of omega-3 lysine salt with DOPC (preparation 1.3) | 6 ml + 4 ml PBS buffer | 2.04 |

Subsequently, the cells were separated by centrifugation (15 min, 4000 rpm, room temperature), and supernatants were withdrawn to analyze for the presence of omega-3 metabolites. The supernatants were diluted with a solvent consisting of a water/acetonitrile mixture (ratio supernatants:solvent was 1:2, solvent composition: 65% $H_2O$, pH8 and 35% MeCN).

The diluted supernatant samples were filtered and then used for the detection of 18-hydroxy-eicosapentaenoic acid (18-HEPE) by LC/ESI-MS analysis (Agilent QQQ 6420, Gemini 3p C6-Phenyl) in positive SIM-Mode at m/z 318 as well as the precursor compound EPA at m/z 302.

In the presence and absence of bile salts, 18-HEPE was formed and detected in the supernatant most effectively, when omega-3 fatty acid was provided to *Bacillus megaterium* DSM 32963 cells as omega-3 lysine salt formulated with phospholipids. The results are summarized in table 6.

TABLE 6 measured 18-HEPE concentrations (mg/l) of culture supernatants in absence and presence of bile acids

| | | 18-HEPE content (mg/l) | | |
| --- | --- | --- | --- | --- |
| Supplement added | bile acids | supernatant of culture | control without cells | -netto- cellular produced |
| PBS buffer | − | 0.0 | 0.0 | 0.0 |
| Omega-3 lysine salt (4.6) | − | >0.2 | >0.3 | 0.0 |
| Omega-3 lysine salt with DOPC (1.3) | − | >0.5 | >0.1; <0.2 | >0.3 |
| Fish oil with DOPC (1.1) | − | >0.05 | 0.0 | >0.05 |
| Omega-3 ethyl ester with DOPC (1.2) | − | 0.0 | >0.1 | 0.0 |
| PBS buffer | + | 0.0 | 0.0 | 0.0 |
| Omega-3 lysine salt with DOPC (1.3) | + | >1.2 | >0.5; <1 | >0.2 |
| Fish oil with DOPC (1.1) | + | 0.0 | 0.0 | 0.0 |
| Omega-3 ethyl ester with DOPC (1.2) | + | 0.0 | 0.0 | 0.0 |

Example 7: Stimulated Expansion of Human Bone Marrow Mesenchymal Stromal Cells by Addition of Phospholipid Dispersed Omega-3 Fatty Acid Salts Human bone marrow mesenchymal stromal cells (MSCs) are used for medical purposes in the form of cell therapies and to derive specific cell and tissue types for tissue engineering, e.g. for the generation of chondrocytes to make in vitro cartilage. In order to do so, suitable medium compositions are required that allow efficient expansion/multiplication of isolated cells. In general, it is assumed that lipids need to be supplemented if serum free, chemically defined media are used. The suitability of the lipid formulations described in this invention to efficiently expand stromal cells was evaluated as described in the following passage.

A chemically defined cell culture medium was prepared as described by Jung et al. (Cytotherapy, 2010; 12: 637-657). The composition of the medium is shown in Table 7.

TABLE 7 composition of chemically defined medium for cultivation of mesenchymal stromal cells

| Ingredient | Concentration applied | |
|---|---|---|
| DMEM/Ham's F-12 medium, 1:1 | | |
| L-glutamine | 1.5 | mM |
| Chemically defined lipid concentrate | 0.1 | % |
| Sodium bicarbonate | 1.725 | g/L |
| HEPES | 4.90 | mM |
| Insulin | 23 | mg/L |
| Human apo- transferrin | 25 | mg/L |
| Putrescine dihydrochloride | 9 | mg/L |
| Progesterone | 5.66 | µg/L |
| Human serum albumin (HSA) | 4 | g/L |
| bFGF | 20 | µg/L |
| TGF-β1 | 10 | µg/L |
| Ascorbic acid | 50 | mg/L |
| Hydrocortisone | 100 | nM |
| Fetuin | 1 | g/L |
| Attachment substrate | 0.1% Gelatine | |

The chemically defined lipid concentrate was obtained by Thermo Fisher Scientific (Catalog no. 11905031) and consisted of a mixture of fatty acids and cholesterol formulated with non-ionic surfactants (Polysorbate 80 and Pluronic F-68).

Two additional batches of this medium were prepared, one without chemically defined lipid concentrate and one where the chemically defined lipid concentrate was replaced by the preparation of omega-3 lysine salt formulated with DOPC (example 1.3). 0.1 ml of liquid preparation was added to 100 ml of cell culture medium, corresponding to a 1000× dilution and resulting in a fatty acid concentration of about 10 mg/l.

Human bone marrow mesenchymal stromal cells derived in chemically defined medium from bone marrow mononuclear cells were obtained from StemCell Technologies, thawed as recommended by the supplier and expanded in the three different medium versions. The medium was inoculated at a cell density of 150 000 cells/ml and cells were expanded in T25 cell culture flasks in a $CO_2$ incubator. The medium was replaced every 2-3 days and cells were passaged before becoming confluent. Cells were detached with Accutase™ (StemCell Technologies), viable cell concentration was determined and fresh medium was inoculated with 150 000 cell/ml at each passage.

Cumulated population doublings (CPD) as an indicator of growth performance, were calculated from the number of passages and the measured cell concentrations. Surprisingly it was found, that the chemically defined lipid concentrate as described in the literature did not have a positive effect on CPD (CPD=4.63) when compared to the medium without added lipids (CPD=4.77). In contrast to that, addition of omega-3 lysine salt formulated with DOPC did have positive effects and resulted in increased CPD of 7.37.

The invention claimed is:

1. A preparation, comprising:
   a dispersion of at least one phospholipid and at least one fatty acid salt of a cation with an anion derived from an omega-3 or omega-6 fatty acid,
   wherein the phospholipid is a deoiled phospholipid comprising a phosphatidylcholine content of greater than 70 weight % and a phosphatidylethanolamine content of lower than 5 weight %.

2. The preparation according to claim 1, wherein the fatty acid is selected from the group consisting of eicosapentaenoic acid (EPA), docosahexaenoic acid (DHA), arachidonic acid (ARA), alpha linolenic acid, stearidonic acid, eicosatetraenoic acid, docosapentaenoic acid, linoleic acid, γ-linolenic acid and a derivative thereof.

3. The preparation according to claim 1, wherein the cation is at least one organic cation derived from the group consisting of lysine, arginine, ornithine and choline.

4. The preparation according to claim 1, wherein the phospholipid is a non-hydrogenated phospholipid having an oleic and/or linoleic acid content of greater than 70 weight % of total fatty acids.

5. The preparation according to claim 1, wherein a mass ratio of the phospholipid to the fatty acid salt is greater than 0.005.

6. The preparation according to claim 1, wherein the preparation is in the form of a powder or a liquid that results in colloidal dispersions with mean particle sizes of smaller than 1 µm when mixed with water at a pH value of between pH 6.5 and 7.5.

7. The preparation according to claim 1, wherein components are finely dispersed in each other so that both phospholipid and fatty acid salts are present and detectable in amounts of 100 µg and smaller.

8. A culture medium comprising the preparation according to claim 1.

9. The culture medium according to claim 8, wherein said culture medium is in liquid form, in form of a gel, a powder, a granulate, a pellet or in form of a tablet.

10. A method for preparing the preparation according to claim 1, the method comprising:
   a. dissolving a phospholipid and a fatty acid salt together in a water-miscible solvent and adding small amounts of water to fully dissolve the salt, thereby obtaining a solution;
   b. adding the solution to an aqueous system to prepare a lipid dispersion;
   c. reducing a particle size of the lipid dispersion to a mean particle size of smaller than 500 nm via sonification or homogenization; and
   d. optionally drying the preparation.

11. A method for preparing the preparation according to claim 1, the method comprising:
   a. dissolving a phospholipid in a water-miscible solvent, thereby obtaining a phospholipid solution;
   b. dissolving the fatty acid salt in an aqueous system and adding the phospholipid solution to the aqueous system to prepare a lipid dispersion;

c. reducing a particle size of the lipid dispersion to a mean particle size of smaller than 500 nm via sonification or homogenization; and d. optionally drying the preparation.

12. The method according to claim 10, wherein the water-miscible solvent is at least one selected from the group consisting of ethanol, glycerol and propylene glycol.

13. A method for providing polyunsaturated fatty acids to cells, tissues, organs or organisms, the method comprising:

contacting the preparation of claim 1 with cells, tissues, organs or organisms.

14. A method for cultivating or stimulating expansion of mesenchymal stem cells, the method comprising:

contacting the preparation of claim 1 with mesenchymal stem cells.

15. A feed or food supplement or a pharmaceutical product, comprising the preparation of claim 1.

16. The preparation according to claim 1, wherein the phospholipid is a deoiled phospholipid comprising a phosphatidylcholine content of greater than 90 weight % and a phosphatidylethanolamine content of lower than 1 weight %.

17. The preparation according to claim 1, wherein the cation is at least one organic cation derived from the group consisting of arginine and ornithine.

18. The preparation according to claim 1, wherein a mass ratio of the phospholipid to the fatty acid salt is greater than 0.39 and less than 3.

* * * * *